(12) United States Patent
Green et al.

(10) Patent No.: US 9,035,246 B2
(45) Date of Patent: *May 19, 2015

(54) ION GUIDE WITH ORTHOGONAL SAMPLING

(71) Applicant: Micromass UK Limited, Wilmslow (GB)

(72) Inventors: Martin Raymond Green, Bowdon (GB); David J. Langridge, Stockport (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/245,292

(22) Filed: Apr. 4, 2014

(65) Prior Publication Data

US 2014/0217278 A1   Aug. 7, 2014

Related U.S. Application Data

(63) Continuation of application No. 14/004,529, filed as application No. PCT/GB2012/050544 on Mar. 13, 2012, now Pat. No. 8,716,660.

(60) Provisional application No. 61/476,866, filed on Apr. 19, 2011.

(30) Foreign Application Priority Data

Mar. 14, 2011  (GB) .................................. 1104220.7

(51) Int. Cl.
  *H01J 49/06* (2006.01)
  *H01J 49/02* (2006.01)
  *H01J 49/00* (2006.01)

(52) U.S. Cl.
  CPC ............. *H01J 49/065* (2013.01); *H01J 49/062* (2013.01); *H01J 49/022* (2013.01); *H01J 49/0031* (2013.01)

(58) Field of Classification Search
  CPC ....... H01J 49/06; H01J 49/061; H01J 49/062; H01J 49/063; H01J 49/065; H01J 49/401; G01N 27/622; G01N 27/624
  USPC .......................................................... 250/287
  See application file for complete search history.

(56) References Cited

U.S. PATENT DOCUMENTS 5,763,878 A * 6/1998 Franzen .................... 250/292
5,939,613 A * 8/1999 Naaman et al. ............. 250/287

(Continued)

FOREIGN PATENT DOCUMENTS

| GB | 2421845 | 7/2006 |
| GB | 2464592 | 4/2010 |
| GB | 2468077 | 8/2010 |

*Primary Examiner* — Jack Berman
(74) *Attorney, Agent, or Firm* — Diederiks & Whitelaw, PLC

(57) ABSTRACT

A mass spectrometer is disclosed comprising a RF ion guide wherein in a mode of operation a continuous, quasi-continuous or pulsed beam of ions is orthogonally sampled from the ion guide and wherein the continuous, quasi-continuous or pulsed beam of ions is not axially trapped or otherwise axially confined within the RF ion guide. The ion guide is maintained, in use, at a pressure selected from the group consisting of: (i) 0.0001-0.001 mbar; (ii) 0.001-0.01 mbar; (iii) 0.01-0.1 mbar; (iv) 0.1-1 mbar; (v) 1-10 mbar; (vi) 10-100 mbar; and (vii) >100 mbar.

24 Claims, 4 Drawing Sheets

(56) References Cited

U.S. PATENT DOCUMENTS

| | | |
|---|---|---|
| 7,385,187 B2 | 6/2008 | Verentchikov et al. |
| 7,388,193 B2 * | 6/2008 | Li ................................. 250/287 |
| 8,716,660 B2 * | 5/2014 | Green et al. ................... 250/292 |
| 2003/0136905 A1 * | 7/2003 | Franzen et al. ................ 250/292 |
| 2003/0146377 A1 | 8/2003 | Miller et al. |
| 2004/0217272 A1 | 11/2004 | Horning et al. |
| 2004/0222369 A1 | 11/2004 | Makarov et al. |
| 2004/0245460 A1 | 12/2004 | Tehlirian et al. |
| 2007/0057178 A1 | 3/2007 | Chernushevich et al. |
| 2009/0014641 A1 | 1/2009 | Bateman et al. |
| 2009/0173880 A1 | 7/2009 | Bateman et al. |
| 2009/0272891 A1 | 11/2009 | Giles et al. |
| 2014/0070087 A1 * | 3/2014 | Giles et al. .................... 250/282 |

* cited by examiner

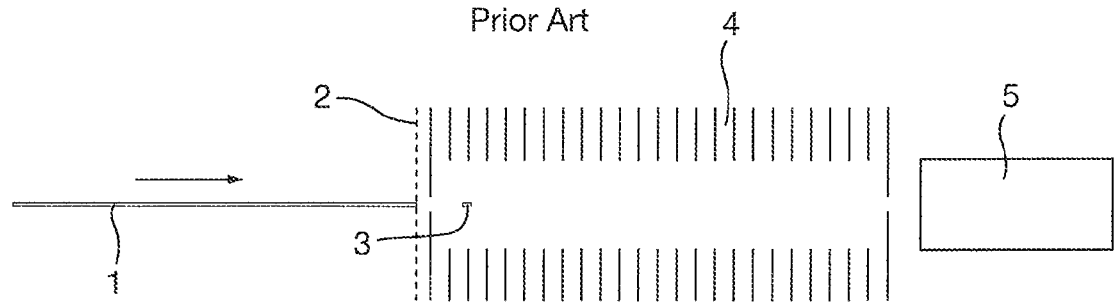
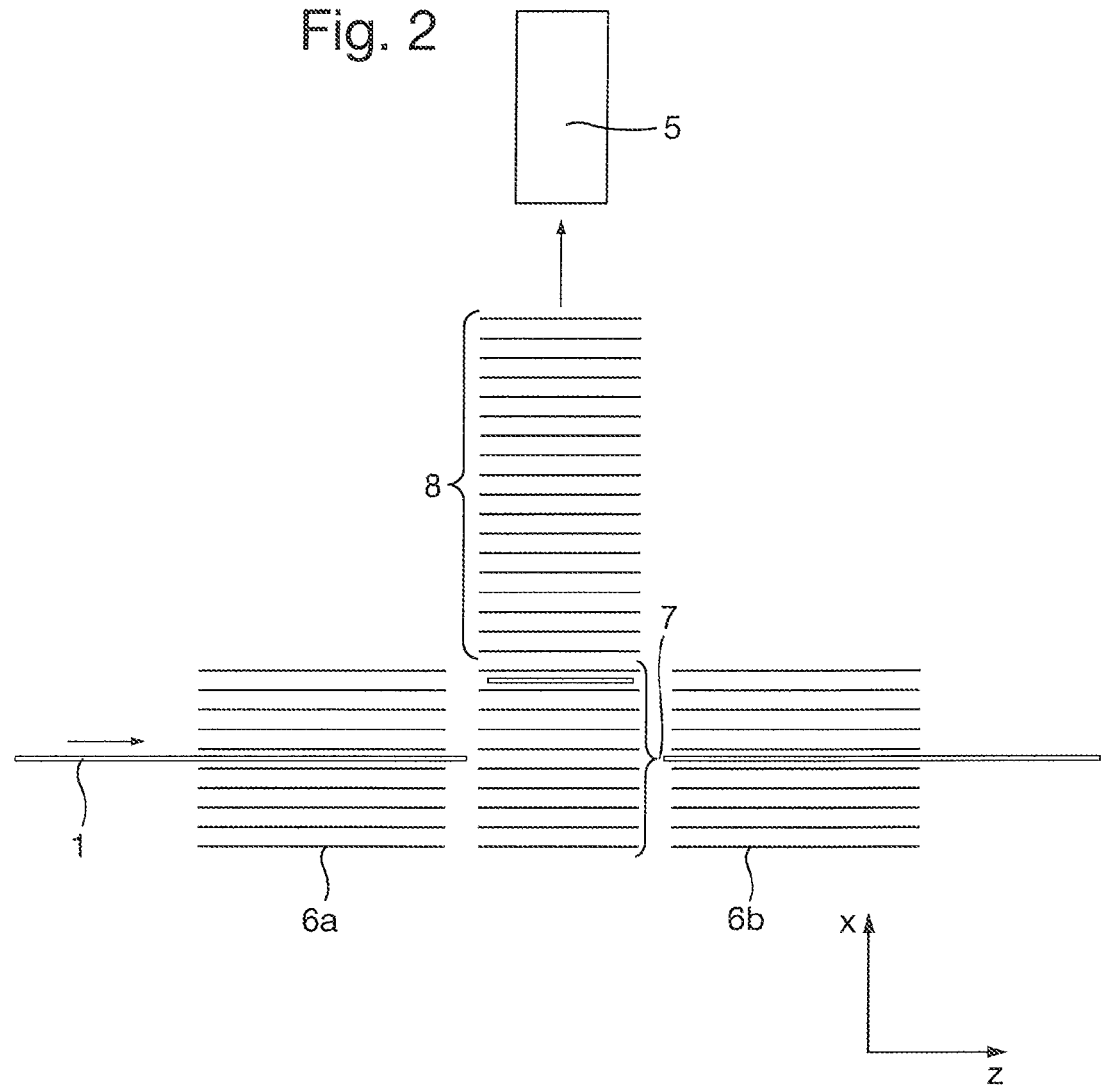

Fig. 3
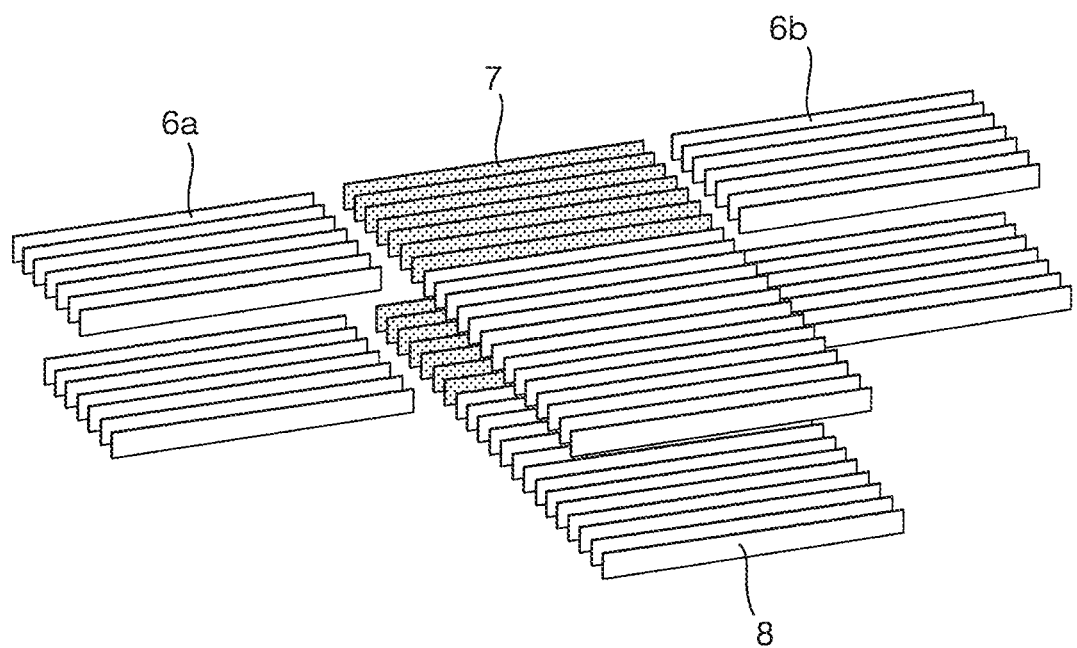
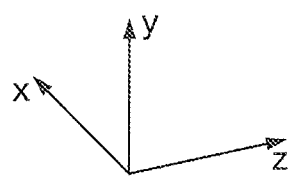

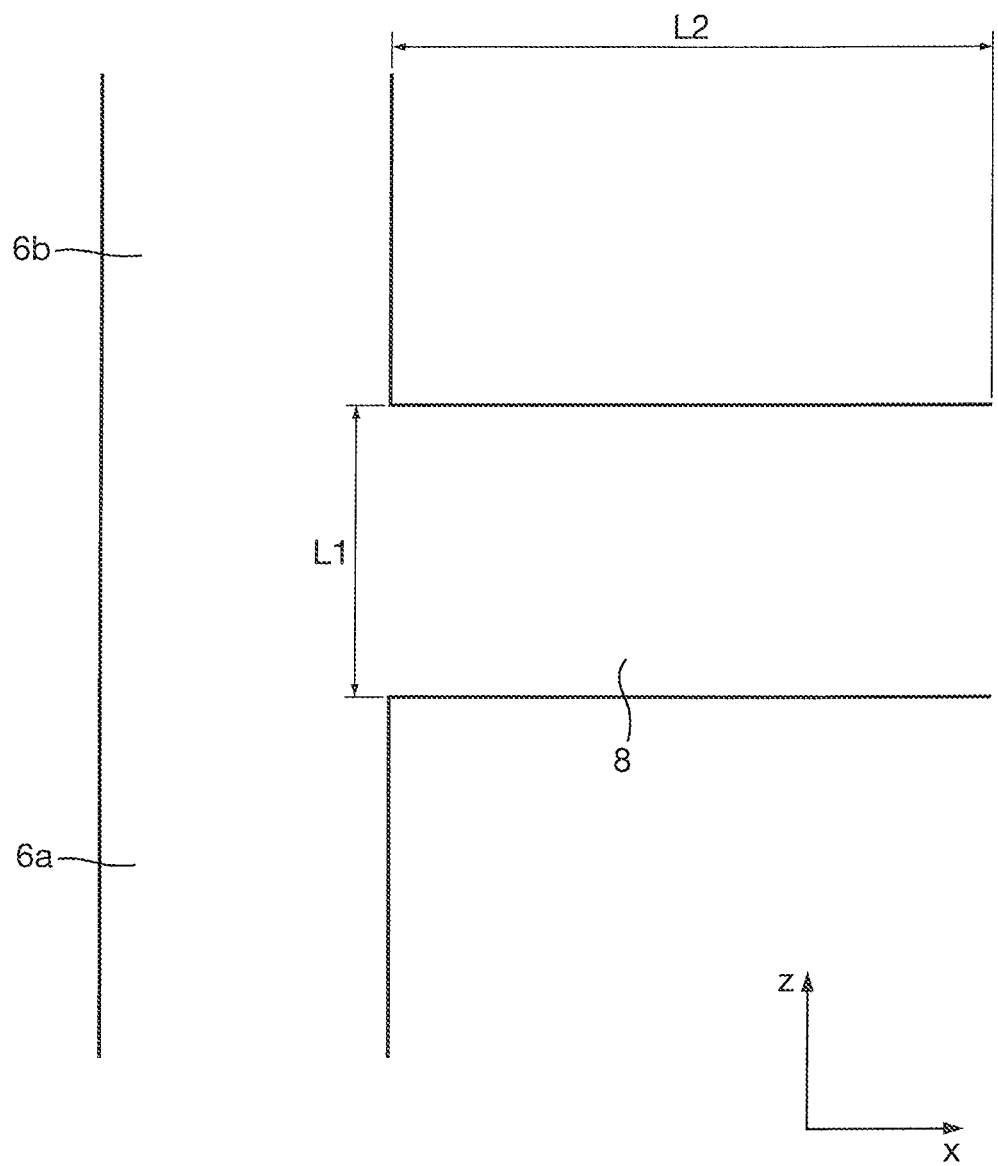

ION GUIDE WITH ORTHOGONAL SAMPLING

CROSS-REFERENCE TO RELATED APPLICATIONS

This application is a continuation of U.S. patent application Ser. No. 14/004,529, filed Sep. 11, 2013, now U.S. Pat. No. 8,716,660 which is the National Stage of International Application No. PCT/GB2012/050544 filed 13 Mar. 2012 which claims priority from and the benefit of U.S. Provisional Patent Application Ser. No. 61/476,866 filed on 19 Apr. 2011 and United Kingdom Patent Application No. 1104220.7 filed on 14 Mar. 2011. The entire contents of these applications are incorporated herein by reference.

BACKGROUND TO PRESENT INVENTION

The present invention relates to a mass spectrometer and a method of mass spectrometry. The preferred embodiment relates to an ion guide and method of guiding ions.

Various separation techniques for separating ions are known and may be broadly divided into two different types. A first type involves performing separation or filtering from a continuous stream of analyte ions. A second type involves analyte ions being delivered in a focussed pulse or as a discontinuous stream of ions.

Devices or techniques which can separate or identify individual components from a continuous stream of analyte ions include RF quadrupole mass filters, magnetic sector mass spectrometers, electrostatic analysers, UV and fluorescence spectrometers and differential ion mobility spectrometers.

Devices or techniques which require discontinuous delivery of analyte ions to separate or identify individual components include gas chromatography, liquid chromatography, Time of Flight mass spectrometers, ion mobility spectrometers, FTICR mass spectrometers and RF and electrostatic ion traps.

In general, for devices or techniques which require discontinuous delivery of analyte ions a period of time must be allowed to elapse between each introduction of a pulse of analyte ions. Often this period of time represents the entire time required to complete the analysis of a prior pulse of analyte ions.

Considering techniques wherein analyte molecules are continuously ionised to produce a continuous beam of ions, such as Electrospray ionisation, a narrow pulse of ions may be generated by gating a small section of the ion beam into the mass spectrometer. The analytical performance of the device is inversely proportional to the width in time of the gated portion of the ion beam. For example, in IMS analysis a typical analysis time may be of the order of 10 ms and a gate width may be of the order of 100 μs. If the remaining incoming ion beam is lost during the 10 ms analytical time then the duty cycle for such a device will be of the order of 1%.

Several approaches have been developed to try to improve the duty cycle for devices such as Ion Mobility Spectrometers ("IMS"). Ions may, for example, be accumulated in an ion storage trap and the ion trap may be used to generate a pulse of ions for analysis. Ions arriving at the ion trap during the analysis time may be accumulated within the ion trap ready for the next analysis period. This method has been used enabling duty cycles approaching 100% to be obtained for ion traps, IMS analysis and Time of Flight analysis.

However, efficient ion trapping with RF confining fields is difficult at pressures approaching atmospheric pressure and also at very low pressures where ions do not lose kinetic energy rapidly due to collisions with background gas molecules. Commercial atmospheric pressure IMS devices do not employ either RF ion traps or RF ion guides.

A second approach to the problem of poor duty cycle is multiplexing wherein ions are pulsed into a mass spectrometer at a frequency faster that the frequency imposed by the total analysis time of the device. This produces complex spectra which need to be de-convolved based on knowledge of the initial gating frequency or encoding pattern. Hadamard transform Time of Flight is an example of this approach.

A third approach commonly employed for Time of Flight mass spectrometry is orthogonal extraction. A relatively large section of an ion beam is extracted orthogonally by application of a sudden voltage pulse. As the energy spread of the beam in the orthogonal direction is relatively low compared with the axial direction, very high resolution time of flight analysis can be realised with duty cycles of the order of 20%-40%.

For time of flight analysis orthogonal extraction of a continuous ion beam is performed at very low pressures to minimise collisions with background gas which would otherwise degrade the performance of the Time of Flight analyser and/or cause collisionally induced fragmentation.

It is desired to provide an improved mass spectrometer and method of mass spectrometry.

SUMMARY OF THE INVENTION

According to an aspect of the present invention there is provided a mass spectrometer comprising:

an RF ion guide comprising a plurality of electrodes wherein in a mode of operation a continuous, quasi-continuous or pulsed beam of ions is orthogonally sampled from the ion guide and wherein the continuous, quasi-continuous or pulsed beam of ions is not axially trapped or otherwise axially confined within the RF ion guide; and a device arranged and adapted to maintain the ion guide at a pressure selected from the group consisting of: (i) 0.0001-0.001 mbar; (ii) 0.001-0.01 mbar; (iii) 0.01-0.1 mbar; (iv) 0.1-1 mbar; (v) 1-10 mbar; (vi) 10-100 mbar; and (vii) >100 mbar.

Ions are confined within the RF ion guide by a radial pseudo-potential which acts to confine ions in at least one radial direction within the ion guide.

The beam of ions is preferably non-mass selectively sampled or otherwise ejected from the ion guide.

The mass spectrometer preferably further comprises a device arranged and adapted to apply a DC potential to at least some of the electrodes in order to cause ions to be orthogonally sampled from the ion guide preferably in a non-mass or non-mass to charge ratio selective manner.

According to a less preferred embodiment the mass spectrometer may further comprise a device arranged and adapted to apply a (small) RF potential in addition to the DC potential to at least some of the electrodes in order to cause ions to be orthogonally sampled from the ion guide.

The mass spectrometer may further comprise a device arranged and adapted to urge ions along at least a portion, or substantially the whole of the axial length of the ion guide. The device is preferably arranged and adapted either:

(i) to apply one or more transient DC voltages or potentials to at least some of the electrodes; and/or (ii) to maintain a DC voltage gradient along at least a portion or substantially the whole of the axial length of the ion guide; and/or (iii) to apply a RF voltage having three or more phases to at least some of the electrodes, wherein different phases of the RF voltage are applied to different electrodes.

According to an embodiment ions may be pre-separated according to a physico-chemical property prior to arriving at said ion guide and/or whilst being transmitted through the ion guide.

According to an embodiment the physico-chemical property may comprise mass or mass to charge ratio. As a result, orthogonally sampling the beam of ions has the effect of selecting ions having masses or mass to charge ratios within a particular mass or mass to charge ratio range.

According to another embodiment the physico-chemical property may comprise ion mobility or differential ion mobility. As a result, orthogonally sampling the beam of ions has the effect of selecting ions having ion mobilities or differential ion mobilities within a particular ion mobility or differential ion mobility range.

The RF ion guide preferably comprises at least 6, 7, 8, 9, 10, 11, 12, 13, 14, 15, 16, 17, 18, 19 or 20 electrodes. A RF voltage is preferably applied to the at least 6, 7, 8, 9, 10, 11, 12, 13, 14, 15, 16, 17, 18, 19 or 20 electrodes.

The ion guide is preferably maintained, in use, at a pressure such that the mean free path of ions within the ion guide is substantially less than the length of the ion guide.

The plurality of electrodes may comprise substantially planar electrodes.

According to another embodiment the plurality of electrodes may comprise rod or ring electrodes.

The continuous, quasi-continuous or pulsed beam of ions is preferably orthogonally sampled so that a portion of the ion beam experiences an electric field in a direction which is substantially orthogonal to the initial direction of the ion beam.

The continuous, quasi-continuous or pulsed beam of ions is preferably orthogonally sampled with a duty cycle selected from the group consisting of (i) <5%; (ii) 5-10%; (ill) 10-15%; (iv) 15-20%; (v) 20-25%; (vi) 25-30%; (vii) 30-35%; (viii) 35-40%; (ix) 40-45%; (x) 45-50%; (xi) 50-55%; (xii) 55-60%; (xiii) 60-65%; (xiv) 65-70%; (xv) 70-75%; (xvi) 75-80%; (xvii) 80-85%; (xviii) 85-90%; (xix) 90-95%; and (xx) >95%.

The mass spectrometer preferably further comprises a device arranged and adapted to apply an AC or RF voltage to the electrodes in order to confine ions within the ion guide in a first direction (y).

The mass spectrometer preferably further comprises a control system, wherein the control system is arranged and adapted in a first mode of operation to apply a DC voltage additionally to the electrodes in order to confine ions within the ion guide in a second different direction (x). The second direction (x) is preferably orthogonal to the first direction (y).

The control system is preferably arranged and adapted to switch the ion guide to operate in a second mode of operation wherein ions are orthogonally sampled from a portion of the ion guide.

The mass spectrometer preferably further comprises an analytical separation device and wherein in the second mode of operation ions are orthogonally sampled from the ion guide and are transmitted to the analytical separation device.

The analytical separation device preferably comprises: (i) a mass or mass to charge ratio separation device; (ii) an ion mobility separation device; or (iii) a differential ion mobility separation device.

The mass spectrometer may further comprise a reaction or collision cell wherein ions are orthogonally sampled from the ion guide and are transmitted to the reaction or collision cell.

Ions within the ion guide may be separated with respect to their ion mobility, mass to charge ratio or differential ion mobility.

According to an embodiment the RF ion guide may comprise a quadrupole rod set, a hexapole rod set, an octopole rod set or a multipole rod set having ten or more rod electrodes.

According to an aspect of the present invention there is provided method of mass spectrometry comprising:

providing a RF ion guide;

passing a continuous, quasi-continuous or pulsed beam of ions through the RF ion guide, wherein the continuous, quasi-continuous or pulsed beam of ions is not axially trapped or otherwise axially confined within the RF ion guide;

orthogonally sampling the continuous, quasi-continuous or pulsed beam of ions; and maintaining the ion guide at a pressure selected from the group consisting of; (i) 0.0001-0.001 mbar; (ii) 0.001-0.01 mbar; (iii) 0.01-0.1 mbar; (iv) 0.1-1 mbar; (v) 1-10 mbar; (vi) 10-100 mbar; and (vii) >100 mbar.

According to an aspect of the present invention there is provided a mass spectrometer comprising:

an RF ion guide comprising a plurality of electrodes wherein in a first mode of operation a DC voltage is applied to the electrodes in order to confine ions radially within the ion guide within a DC potential well and wherein in a second mode of operation the DC potential applied to the electrodes is varied so that ions are orthogonally sampled from the ion guide.

According to the preferred embodiment ions are not confined axially within the ion guide during the first mode of operation.

According to an aspect of the present invention there is provided a method of mass spectrometry comprising:

providing an RF ion guide comprising a plurality of electrodes;

applying a DC voltage to the electrodes in order to confine ions radially within the ion guide within a DC potential well; and varying the DC potential applied to the electrodes so that ions are orthogonally sampled from the ion guide.

According to the preferred embodiment ions are not confined axially within the ion guide when ions are orthogonally sampled.

According to an aspect of the present invention there is provided a mass spectrometer comprising:

an ion guide comprising a drift tube wherein in a mode of operation a continuous, quasi-continuous or pulsed beam of ions is orthogonally sampled from the ion guide and wherein the continuous, quasi-continuous or pulsed beam of ions is not axially trapped or otherwise axially confined within the ion guide; and a device arranged and adapted to maintain the ion guide at a pressure selected from the group consisting of: (i) 0.0001-0.001 mbar; (ii) 0.001-0.01 mbar; (iii) 0.01-0.1 mbar; (iv) 0.1-1 mbar; (v) 1-10 mbar; (vi) 10-100 mbar; and (vii) >100 mbar.

According to the preferred embodiment no RF voltage is applied to the drift tube.

According to an aspect of the present invention there is provided a method of mass spectrometry comprising:

providing an ion guide comprising a drift tube;

passing a continuous, quasi-continuous or pulsed beam of ions through the ion guide, wherein the continuous, quasi-continuous or pulsed beam of ions is not axially trapped or otherwise axially confined within the ion guide;

orthogonally sampling the continuous, quasi-continuous or pulsed beam of ions; and maintaining the ion guide at a pressure selected from the group consisting of: (i) 0.0001-0.001 mbar; (ii) 0.001-0.01 mbar; (iii) 0.01-0.1 mbar; (iv) 0.1-1 mbar; (v) 1-10 mbar; (vi) 10-100 mbar; and (vii) >100 mbar.

According to the preferred embodiment no RF voltage is applied to the drift tube.

The preferred embodiment preferably enables orthogonal sampling of a first or primary ion beam at an elevated pressure. The pressure is preferably such that the mean free path of an ion is substantially less than the length of the high pressure region.

The orthogonal sampling of the ion beam is preferably performed in an ion guide wherein ions are confined within the ion guide by an RF voltage.

However, less preferred embodiments are also contemplated wherein orthogonal sampling of an ion beam may be performed from a drift tube with no RF confinement.

Ions are preferably orthogonally sampled into a further analytical separation device which may be arranged to separate ions either on the basis of their mass to charge ratio or their ion mobility.

Ions may be orthogonally sampled into a reaction or collision cell.

The first or primary ion beam is preferably continuous or discontinuous.

The first or primary ion beam may be separated with respect to ion mobility or with respect to mass to charge ratio.

The first or primary ion beam may be separated or filtered with respect to differential ion mobility.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical ionisation ("APCI") ion source; (iv) a Matrix Assisted Laser Desorption Ionisation ("MALDI") ion source; (v) a Laser Desorption ionisation ("LDI") ion source; (vi) an Atmospheric Pressure Ionisation ("API") ion source; (vii) a Desorption ionisation on Silicon ("DIOS") ion source; (viii) an Electron impact ("EI") ion source; (ix) a Chemical ionisation ("CI") ion source; (x) a Field ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions: (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser: (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap: (iv) a Penning ion trap; (v) an ion trap (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either:

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment one or more transient DC voltages or potentials or the one or more DC voltage or potential waveforms may be applied to the electrodes of the ion guide to create: (i) a potential hill or barrier; (ii) a potential well; (iii) multiple potential hills or barriers; (iv) multiple potential wells; (v) a combination of a potential hill or barrier and a potential well; or (vi) a combination of multiple potential hills or barriers and multiple potential wells.

The one or more transient DC voltage or potential waveforms preferably comprise a repeating waveform or square wave.

An RF voltage is preferably applied to the electrodes of the ion guide and preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; (xi) 500-550 V peak to peak; (xxii) 550-600 V peak to peak; (xxiii) 600-650 V peak to peak; (xxiv) 650-700 V peak to peak; (xxv) 700-750 V peak to peak; (xxvi) 750-800 V peak to peak; (xxvii) 800-850 V peak to peak; (xxviii) 850-900 V peak to peak; (xxix) 900-950 V peak to peak; (xxx) 950-1000 V peak to peak; and (xxxi) >1000 V peak to peak.

The RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-100 MHz; and (xxv) >10.0 MHz.

The ion guide is preferably maintained at a pressure selected from the group comprising: (i) >0.001 mbar; (ii) >0.01 mbar; (iii) >0.1 mbar; (iv) >1 mbar; (v) >10 mbar; (vi) >100 mbar; (vii) 0.001-0.01 mbar; (viii) 0.01-0.1 mbar; (ix) 0.1-1 mbar; (x) 1-10 mbar; and (xi) 10-100 mbar.

BRIEF DESCRIPTION OF THE DRAWINGS

Various embodiments of the present invention will now be described, by way of example only, together with other arrangements given for illustrative purposes only and with reference to the accompanying drawings in which:

FIG. 1 shows a conventional arrangement wherein ions are gated into a high pressure analytical device;

FIG. 2 shows an ion guide according to a preferred embodiment of the present invention;

FIG. 3 shows a three dimensional representation of the ion guide shown in FIG. 2 according to an embodiment of the present invention;

FIG. 5 shows a simplified schematic diagram of an ion guide according to a preferred embodiment of the present invention.

DETAILED DESCRIPTION OF THE PREFERRED EMBODIMENT

Figure 4A:
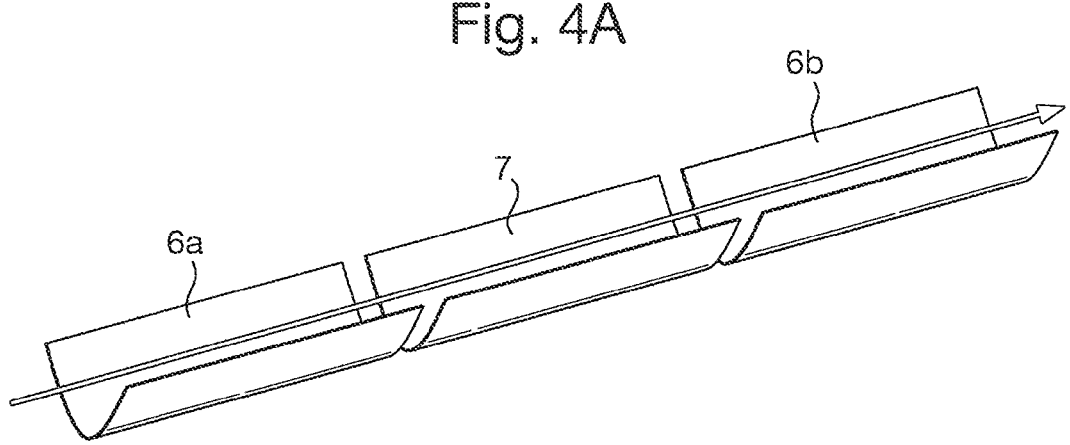
FIG. 4A shows the form of a DC confining potential applied to the embodiment shown in FIG. 3 prior to causing at least some ions to be sampled orthogonally and FIG. 4B shows the form of the DC potential applied to the ion guide shown in FIG. 3 in order to sample at least some ions orthogonally.

A conventional mass spectrometer will first be described with reference to FIG. 1. FIG. 1 shows a conventional mass spectrometer wherein a primary ion beam 1 is prevented from entering a high pressure analytical device 4 by an ion gate 2. The ion gate 2 is opened for a sufficient period of time so as to allow a narrow pulse of ions 3 to enter into the analytical device 4. As ions traverse the analytical device 4 the ions separate temporally dependent upon either their ion mobility or their mass to charge ratio. The ions are then transmitted to a further downstream analyser, a fragmentation device or an ion detector 5 which is arranged downstream of the analytical device 4.

FIG. 2 shows an ion guide according to a preferred embodiment of the present invention and FIG. 3 shows a corresponding three dimensional view of the ion guide. According to the preferred embodiment a continuous, quasi-continuous or pulsed beam of ions 1 is preferably arranged to enter an RF ion guide 6a,7,6b. The ion guide 6a,7,6b preferably comprises three sections 6a,7,6b and a fourth section 8.

According to the preferred embodiment the electrodes of a first ion guide section 6a and the electrodes of a third ion guide section 6b are preferably supplied with a RF potential wherein adjacent plates or electrodes are preferably supplied with a RF voltage which is 180° out of phase. The applied RF potential results in a pseudo-potential force which effectively contains or confines ions in the y (vertical) direction (see FIG. 3) within the first ion guide section 6a and within the third ion guide section 6b.

An intermediate second ion guide section 7 is preferably provided between the first ion guide section 6a and the third ion guide section 6b. The second ion guide section 7 may be operated in two different modes of operation and may be operated either as an ion guide section or as an orthogonal acceleration region.

A fourth ion guide section 8 is preferably provided which may be operated either as an ion guide to transmit ions to a further device or as an analytical separation region. The fourth ion guide section 8 is preferably arranged adjacent the intermediate second ion guide section 7, and preferably receives ions which have been orthogonally sampled from the intermediate second ion guide section 7.

In a transmission or ion guide mode of operation the electrodes of the first ion guide section 6a, the electrodes of the second ion guide section 7 and the electrodes of the third ion guide section 6b are preferably supplied with opposite phases of a RF voltage as described above so that ions are confined within the first, second and third ion guide sections 6a,7,6b in the y direction. In addition, a DC potential is also preferably applied to the electrodes forming the first, second and third ion guide sections 6a,7,6b so as to create a predominantly DC confining force in the x (horizontal) direction. The form of the confining DC well in the ion transmission or ion guiding mode is shown in FIG. 4A. In this mode of operation, ions preferably pass unhindered through the first, second and third ion guiding regions 6a,7,6b of the device in the z (axial) direction. Ions may be urged in the z (axial) direction by the application of a DC or pseudo-potential field or by applying a DC or pseudo-potential travelling wave to the electrodes of the ion guides 6a,7,6b.

Figure 4B:
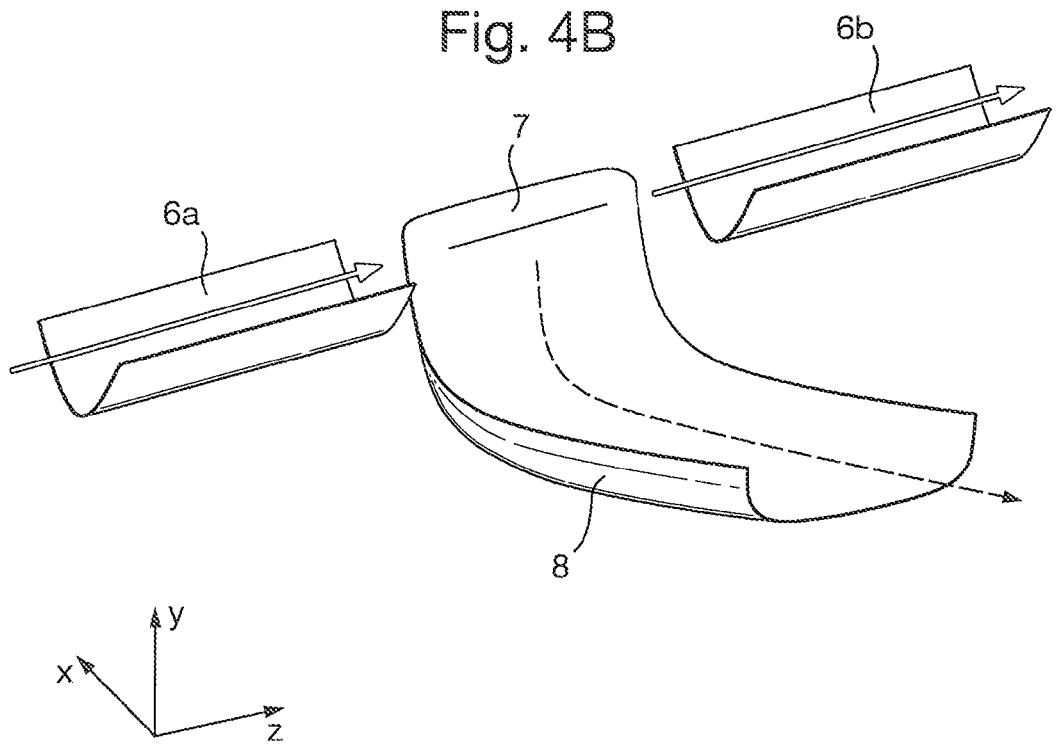

FIG. 4B shows the DC field within the ion guide according to the preferred embodiment during an orthogonal extraction mode of operation. In this mode of operation the second ion guide section 7 is preferably supplied with a DC field which preferably acts to extract a portion of the ion beam in an orthogonal manner into the fourth ion guide section 8. The fourth ion guide section 8 may be supplied with a static field or a travelling wave in order to urge ions along the axis of the fourth ion guide section 8.

Once a portion of the ion beam has exited the second ion guide section 7 and has entered the fourth ion guide section 8 then the DC voltages applied to the electrodes of the first ion guide section 6a, the second ion guide section 7 and the third ion guide section 6b may be restored to those shown in FIG. 4A. The ion beam may then be allowed to travel through the first and second ion guide sections 6a,7 in order to re-populate the orthogonal extraction region of the second ion guide section 7.

The confining RF and DC fields are preferably maintained in the fourth region or ion guide section 8 during the re-population period.

Ions which have been extracted into the fourth ion guide section 8 may be transmitted to another analytical device or to an ion detector. The fourth ion guide section 8 may itself comprise an analytical device. For example, the fourth ion guide section 8 may comprise an ion mobility separation device. Ions which have been orthogonally injected into the fourth ion guide section 8 or ion mobility separation device may be urged through the fourth ion guide section 8 or ion mobility spectrometer and through a drift gas by application of a DC field or travelling wave to the electrodes forming the fourth ion guide section 8. The time taken for ions to exit the fourth ion guide section or ion mobility separator device 8 is preferably related to the effective collision cross section of the analyte ions. As ions travel along the fourth ion guide section 8 they are preferably confined in the y (vertical) direction by a pseudo-potential force due to the applied RF potential and in the z-direction by a DC force or potential well.

In the preferred embodiment the first ion guide section 6a, the second ion guide section 7, the third ion guide section 6b and the fourth ion guide section 8 may be maintained at effectively the same pressure. However, other embodiments are contemplated wherein the pressure and/or the composition of the buffer gas in the first ion guide section 6a and/or in the second ion guide section 7 and/or in the third ion guide section 6b and/or in the fourth ion guide section 8 may be different.

If it is assumed that the pressure and buffer gas composition are identical in the first ion guide section 6a, the second ion guide section 7, the third ion guide section 6b and the fourth ion guide section 8 and that the field urging ions through the first ion guide section 6a, the second ion guide 7 and the third ion guide section 6b in the axial or z-direction and in the x-direction of the fourth ion guide section 8 are identical, then analyte ions will travel through these regions at a velocity $V_d$ related to their ion mobility:

$$V_d \propto KE \qquad (1)$$

wherein $V_d$ is the velocity of the ions, K is the mobility and E is the electric field.

FIGS. 4A and 4B show a simplified schematic of the preferred device. With reference to FIG. 5, the length of a IMS separation region formed in the fourth ion guide section 8 may be defined as being L2. The length of the section of the ion beam which is orthogonally sampled from the second ion guide section 7 is L1. If the velocity of the ions in the continuous, quasi-continuous or pulsed beam is the same as the velocity of the ions in the ion mobility separation ion guide section 8, then the maximum duty cycle $D_1$ for a given analyte is given by:

$$D_i = \frac{L1}{L2} \cdot \frac{K_{min}}{K_1} \qquad (2)$$

wherein $K_{min}$ is the lowest ion mobility associated with an analyte ion present in the ion beam and $K_1$ is the ion mobility associated with a particular analyte ion of interest.

Other modes of operation are contemplated which enable the duty cycle to be improved. For example, the field in the axial or z direction $E_z$ may be different to the field in the separation device or fourth ion guide section 8 in the x direction $E_x$. If the field in the ion guide in the axial or z direction is arranged such that:

$$E_z = \frac{L1}{L2} \cdot E_x \qquad (3)$$

then the maximum duty cycle $D_2$ is given by:

$$D_2 = \frac{K_{min}}{K} \qquad (4)$$

This results in a further improvement in duty cycle.

In another mode of operation a travelling wave or one or more transient DC voltages may be applied to the electrodes forming the first ion guide section 6a and/or the second ion guide section 7 and/or the third ion guide section 6b in the axial or z direction and may be arranged to effectively partition a continuous ion beam. All the ions may then be transported at the velocity of the travelling wave. The velocity of the travelling wave may be arranged such that the extraction region L1 becomes populated with all the analyte ions at the time of completion of the previous analytical scan of the fourth ion guide section 8 and immediately prior to an orthogonal extraction pulse. As a result, it is possible to achieve a duty cycle approaching 100%.

In another embodiment ions may be carried at constant velocity entrained in a stream of buffer gas passing in the axial or z direction and may be sampled orthogonally with high duty cycle.

It should be noted that these are maximum theoretical duty cycle calculations. In practice the duty cycle may be reduced due to effects such as ion losses in the first ion guide section 6a during the period in which the extraction field is ON and ion losses during transfer of ions into the second device during orthogonal extraction.

An important aspect of the preferred embodiment is that gains in duty cycle may be made without compromising the performance of the analytical separation. The primary ion beam may be arranged to have a low spatial and energy spread in the direction of orthogonal sampling. In a system where ions are gated into the analytical region, gains in duty cycle made by increasing the gate time width will result in loss in analytical performance. Narrowing or focussing of the ion beam in the direction of orthogonal ejection is assisted in a RF or RF/DC confined ion guide by collisional cooling of ions as a result of collisions with the background gas. Ions may achieve near thermal energy during progress through such ion guides and are confined to the minima of any confining potential well.

Although the preferred embodiment has been described using an RF ion guide, the same principle may be used to improve the duty cycle using a conventional drift tube with no RF confining field according to less preferred embodiments.

Other geometries of RF ion guide are contemplated including, for example, RF ring stacks and RF rod sets with orthogonal extraction regions.

Further areas of orthogonal sampling may be provided in the first ion guide section 6a and/or the second ion guide section 7 and/or the third ion guide section 6b.

Orthogonal sampling may be performed from the fourth ion guide section 8 during analytical separation. For example, the fourth ion guide section 8 may separate ions with respect to mass to charge ratio. A narrow mass to charge ratio region may then be orthogonally sampled from the fourth ion guide 8 into another analytical device to perform IMS separation of the ions within the sampled mass range. Thus IMS-MS or MS-IMS or IMS-IMS may be performed.

The first ion guide section 6a may itself be an analytical device such as a mass filter or differential ion mobility filter.

Ions may be pulsed into the first ion guide section 6a from a pulsed ion source or from an ion trap and separation of the pulse of ions with respect to mass to charge ratio or ion mobility may be performed within the first ion guide section 6a. Multiple dimensions of separation may therefore be performed.

In a mode of operation the orthogonal acceleration pulse may be synchronised to the release of ions from an ion trap resulting in 100% transmission for ions of a specific mass to charge ratio or ion mobility value.

In addition, orthogonal sampling of the beam may be combined with multiplexing approaches such that ions may be orthogonally sampled from and/or injected into the first ion guide section 6a at a higher frequency than that imposed by the total analysis time of a further analytical device or devices downstream of the fourth ion guiding section 8. The resultant complex spectra produced may be de-convolved based on knowledge of the initial orthogonal sampling frequency or encoding pattern.

Ions which are not orthogonally accelerated from an ion guide may be transmitted thorough the ion guide to another downstream analyser of detector.

The orthogonal extraction pulse may be arranged to vary with time to allow a degree of spatial focussing of the sampled ion beam. This allows the resolution of a subsequent analytical device to be improved.

The axial force urging ions along each ion guide may be arranged to vary in amplitude or speed (in the case of a travelling wave) with time or with position within the ion guide.

Many approaches which have been applied to orthogonal time of flight spectrometry to improve duty cycle are also applicable to orthogonal sampling within the higher pressure device according to an embodiment of the present invention as described above. For example, ions may be delivered mass selectively into the first ion guide section 6a over a short period of time in sequence from high mass to charge ratio to low mass to charge ratio. If the first ion guide section 6a is itself arranged to be a mass selective device wherein ions with low mass to charge ratios have higher velocities through the device than ions with higher mass to charge ratios, then the mass selective release of ions from the ion trap may be matched to the mass selective separation within the ion guide such that ions of all mass to charge ratio values coincide at the orthogonal sampling region 7 at the same time. In this way 100% duty for ions of all mass to charge ratio values or a wide range of mass to charge ratio values may be realised. Due to the correlation between mass to charge ratio and ion mobility for ions of the same charge state, a similar effect may be achieved by matching the release of ions from an ion trap to the progress of ions through the first ion guide section 6a acting as an ion mobility separator. In addition, ions may be released from the trap in order of mobility their arrival synchronised to orthogonal sampling to realise similar duty cycle improvements.

Alternatively, if ions are delivered mass selectively to the first ion guide section 6a and this mass separation is retained as ions are transported through this region, then repetitive orthogonal sampling of the ions may be synchronised to the ion injection such that ions from each mass to charge ratio range are effectively sampled with 100% efficiency.

This same effect may be achieved if ions are pulsed into the first ion guide section 6a in a non-mass selective manner and the first ion guide section 6a is itself a mass or ion mobility separator. Multiple orthogonal sampling events, synchronised to the initial introduction of ions, may be performed. Each orthogonal sampling event results in different mass to charge ratio or mobility ranges being injected into the downstream analytical device. The result is 100% efficiency for ions of all mass to charge ratio or ion mobility values.

Although the present invention has been described with reference to the preferred embodiments, it will be understood by those skilled in the art that various changes in form and detail may be made without departing from the scope of the invention as set forth in the accompanying claims.

The invention claimed is:

1. A mass spectrometer comprising:
an RF ion guide comprising a plurality of electrodes wherein in a mode of operation ions are orthogonally sampled from said ion guide and wherein said ions are not axially trapped or otherwise axially confined within said RF ion guide;
a device arranged and adapted to apply an AC or RF voltage to said electrodes in order to confine ions within said ion guide in a first direction (y); and
a control system, wherein said control system is arranged and adapted in a first mode of operation to apply a DC voltage additionally to said electrodes in order to confine ions within said ion guide in a second different direction (x);
wherein said control system is arranged and adapted to switch said ion guide to operate in a second mode of operation wherein ions are orthogonally sampled from a portion of said ion guide.

2. A mass spectrometer as claimed in claim 1, wherein said ions are non-mass selectively sampled or otherwise ejected from said ion guide.

3. A mass spectrometer as claimed in claim 1, further comprising a device arranged and adapted to apply a DC potential to at least some of said electrodes in order to cause ions to be orthogonally sampled from said ion guide.

4. A mass spectrometer as claimed in claim 3, further comprising a device arranged and adapted to apply an RF potential in addition to said DC potential to at least some of said electrodes in order to cause ions to be orthogonally sampled from said ion guide.

5. A mass spectrometer as claimed in claim 1, further comprising a device arranged and adapted to urge ions along at least a portion or substantially all of an axial length of said ion guide.

6. A mass spectrometer as claimed in claim 5, wherein said device arranged and adapted to urge ions along at least a portion or substantially all of the axial length of said ion guide is arranged and adapted either:

(i) to apply one or more transient DC voltages or potentials to at least some of said electrodes; or (ii) to maintain a DC voltage gradient along at least a portion or substantially all of the axial length of said ion guide; or (iii) to apply a RF voltage having three or more phases to at least some of said electrodes, wherein different phases of said RF voltage are applied to different electrodes.

7. A mass spectrometer as claimed in claim 1, wherein ions are pre-separated according to a physico-chemical property prior to arriving at said ion guide or whilst being transmitted through said ion guide.

8. A mass spectrometer as claimed in claim 7, wherein said physico-chemical property comprises mass or mass to charge ratio.

9. A mass spectrometer as claimed in claim 8, wherein orthogonally sampling said ions has the effect of selecting ions having masses or mass to charge ratios within a particular mass or mass to charge ratio range.

10. A mass spectrometer as claimed in claim 7, wherein said physico-chemical property comprises ion mobility or differential ion mobility.

11. A mass spectrometer as claimed in claim 10, wherein orthogonally sampling said ions has the effect of selecting ions having ion mobilities or differential ion mobilities within a particular ion mobility or differential ion mobility range.

12. A mass spectrometer as claimed in claim 1, wherein said RF ion guide comprises at least 6, 7, 8, 9, 10, 11, 12, 13, 14, 15, 16, 17, 18, 19 or 20 electrodes, and wherein a RF voltage is applied, in use, to said at least 6, 7, 8, 9, 10, 11, 12, 13, 14, 15, 16, 17, 18, 19 or 20 electrodes.

13. A mass spectrometer as claimed in claim 1, wherein said ion guide is maintained, in use, at a pressure such that a mean free path of ions within said ion guide is substantially less than the length of said ion guide.

14. A mass spectrometer as claimed in claim 1, wherein said plurality of electrodes comprise substantially planar electrodes.

15. A mass spectrometer as claimed in claim 1, wherein said plurality of electrodes comprise rod or ring electrodes.

16. A mass spectrometer as claimed in claim 1, wherein said ions are orthogonally sampled as an ion beam so that a portion of said ion beam experiences an electric field in a direction which is substantially orthogonal to an initial direction of said ion beam.

17. A mass spectrometer as claimed in claim 1, wherein ions are orthogonally sampled with a duty cycle selected from the group consisting of: (i) <5%; (ii) 5-10%; (iii) 10-15%; (iv) 15-20%; (v) 20-25%; (vi) 25-30%; (vii) 30-35%; (viii) 35-40%; (ix) 40-45%; (x) 45-50%; and (xi) 50-55%; (xii) 55-60%; (xiii) 60-65%; (xiv) 65-70%; (xv) 70-75%; (xvi) 75-80%; (xvii) 80-85%; (xviii) 85-90%; (xix) 90-95%; and (xx) >95%.

18. A mass spectrometer as claimed in claim 1, further comprising a device arranged and adapted to maintain the ion guide at a pressure selected from the group consisting of: (i) 0.0001-0.001 mbar; (ii) 0.001-0.01 mbar; (iii) 0.01-0.1 mbar; (iv) 0.1-1 mbar; (v) 1-10 mbar; (vi) 10-100 mbar; and (vii) >100 mbar.

19. A mass spectrometer as claimed in claim 1, further comprising an analytical separation device and wherein in a second mode of operation ions are orthogonally sampled from said ion guide and are transmitted to said analytical separation device.

20. A mass spectrometer as claimed in claim 19, wherein said analytical separation device comprises: (i) a mass or mass to charge ratio separation device; (ii) an ion mobility separation device; or (iii) a differential ion mobility separation device.

21. A mass spectrometer as claimed in claim 1, further comprising a reaction or collision cell and wherein ions are orthogonally sampled from said ion guide and are transmitted to said reaction or collision cell.

22. A mass spectrometer as claimed in claim 1, wherein ions within said ion guide are separated with respect to their ion mobility, mass to charge ratio or differential ion mobility.

23. A mass spectrometer as claimed in claim 1, wherein said RF ion guide comprises a quadrupole rod set, a hexapole rod set, an octopole rod set or a multipole rod set having ten or more rod electrodes.

24. A method of mass spectrometry comprising:
providing an RF ion guide comprising a plurality of electrodes;
passing ions through said RF ion guide, wherein said ions are not axially trapped or otherwise axially confined within said RF ion guide;
applying an AC or RF voltage to said electrodes in order to confine ions within said RF ion guide in a first direction (y);
applying in a first mode of operation a DC voltage additionally to said electrodes in order to confine ions within said RF ion guide in a second different direction (x); and
orthogonally sampling said ions from a portion of said RF ion guide in a second mode of operation.

* * * * *